United States Patent [19]
Honkanen et al.

[11] Patent Number: 5,219,357
[45] Date of Patent: Jun. 15, 1993

[54] MICRO-INSTRUMENT

[75] Inventors: George P. Honkanen, North Scituate; Roger M. Burke, Whitman, both of Mass.

[73] Assignee: TNCO, Inc., Whitman, Mass.

[21] Appl. No.: 817,886

[22] Filed: Jan. 3, 1992

Related U.S. Application Data

[63] Continuation-in-part of Ser. No. 531,785, May 31, 1990, Pat. No. 5,152,780.

[51] Int. Cl.[5] .............................................. A61B 17/28
[52] U.S. Cl. .................................... 606/205; 606/174; 128/751
[58] Field of Search ............... 606/167, 170, 176, 205; 604/22; 128/750-754

[56] References Cited

U.S. PATENT DOCUMENTS 4,887,612 12/1989 Esser et al. ........................ 606/174

FOREIGN PATENT DOCUMENTS 0050053 9/1911 Fed. Rep. of Germany ...... 606/174

Primary Examiner—C. Fred Rosenbaum
Assistant Examiner—William Lewis
Attorney, Agent, or Firm—Jerry Cohen; Harvey Kaye; Edwin H. Paul

[57] ABSTRACT

An endoscopic surgical tool (10, FIG. 1) with a single moveable inner tip (22), and a fixed outer tip (12) pivotably interacting via an integral essentially-hourglass-form pivot extension of both walls of the outer tip and an engaging channel (24) of the inner tip(s), articulated by a link with an integral stud and also realizable as with dual moveable inner tips (22A, 22B/FIG. 6), pivotably interacting with respective end-to-end adjacent essentially-hourglass-form sections of a pivot that is an integral extension of the outer tip.

10 Claims, 11 Drawing Sheets

VIEW C

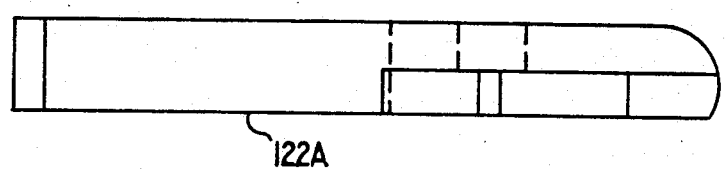
FIG. 10
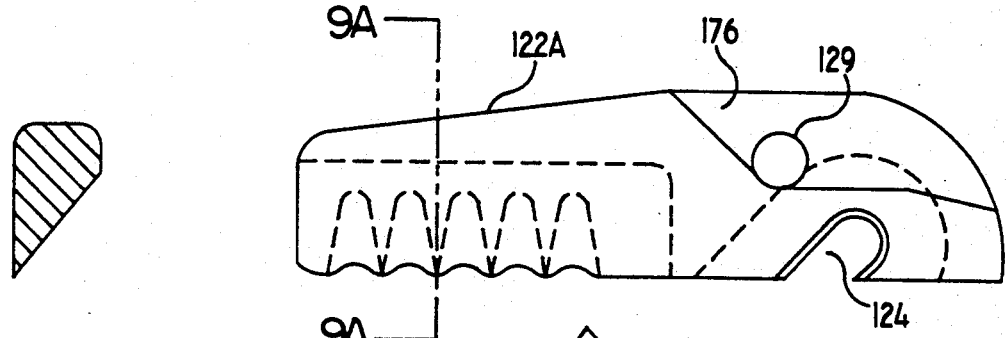
FIG. 9A
FIG. 9
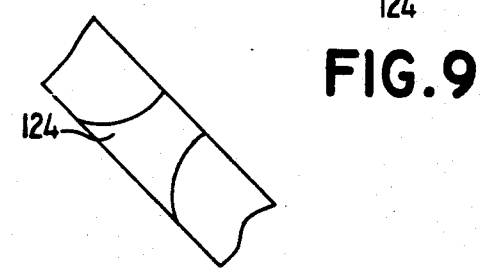
FIG. 9B

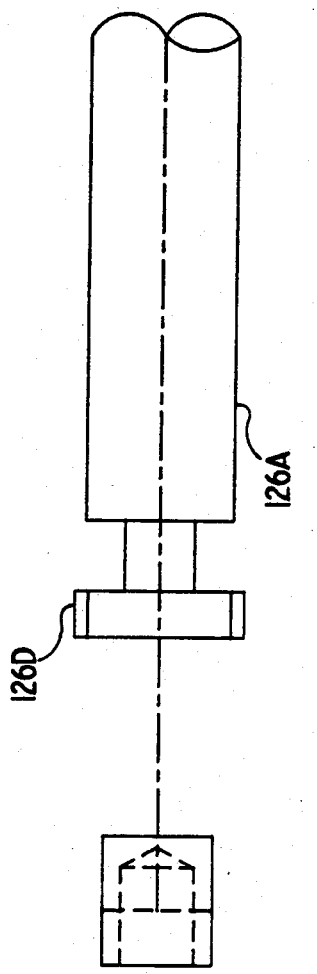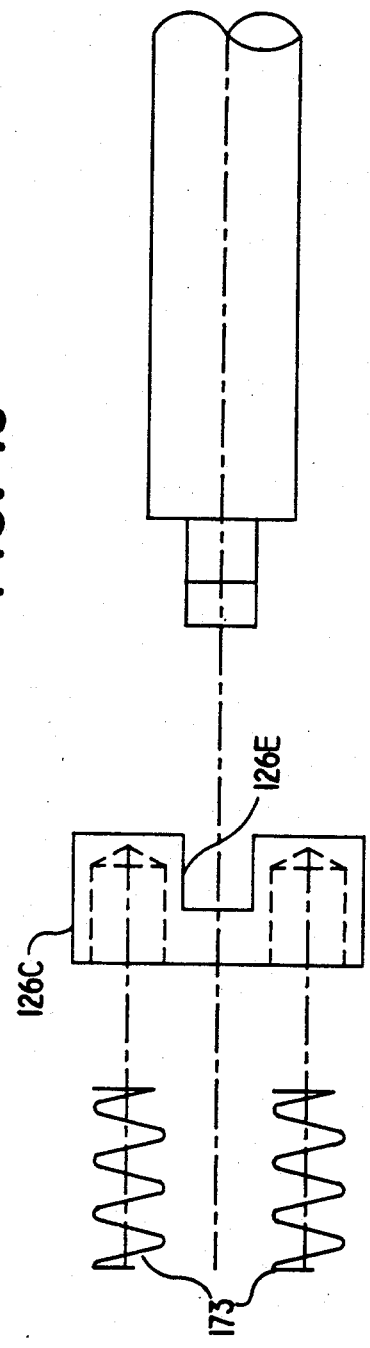
FIG. 15
FIG. 14

MICRO-INSTRUMENT

CROSS REFERENCE TO RELATED APPLICATION

This application is a continuation-in-part of our copending application, Ser. No. 07/531,785, filed May 31, 1990, now U.S. Pat. No. 5,152,780.

BACKGROUND OF THE INVENTION

The present invention relates to micro-instrumentation, i.e. articulating hand held instruments used in micro-surgery, electronic micro-assembly and like applications, for grasping, cutting, punching out, probing, etc. The instruments can comprise scissor-handle-actuators, so-called cigar handle linear or rotary activators, or other actuators, with push or pull force application design modes.

The following discussion of the invention focusses on instruments required for endoscopic usage (minimally invasive procedures) and more particularly punches, scissors and graspers used in temporal-mandibular joint (TMJ) surgery and in laparoscopic surgical procedures. However, the invention is also applicable to other surgical instruments and non-surgical instruments.

Recent generations of enhanced miniaturization of endoscopic instruments have encountered the structural limits of thin cross-sections. As the tip area of such instruments is reduced, the likelihood of breakage and/or the need to reduce applied force becomes evident. The high strength and toughness of advanced metal alloys have not overcome this problem.

It is a principal object of the invention to provide micro-instruments of the classes described above of superior strength. It is a further object of the present invention to provide micro-instruments of the classes described above with reduced tip cross-section dimensions with a rigidity, stability and low vulnerability to breakage heretofore found only in larger instruments.

It is a further object of the present invention to provide micro-instruments of the classes described above with a characteristic that upon a breakage while in use, there is minimal probability of pieces separating from the main body of the instrument.

It is a further and related object of the invention to enable a new level of miniaturization of such instruments and to enable the existence of interlocking type graspers at such new level (as well as punches, scissors and other cutters).

It is a further object of the invention to achieve the previous objects with ease of manufacturability.

SUMMARY OF THE INVENTION

The objects of the invention are realized through the invention's provision of the said instruments in a miniaturized form with articulating handle means (of rod or scissors grip forms or other forms) and elongated probe means extending therefrom, with an elongated actuating linkage portion and a tip portion at the probe end distal from the handle.

The handle portion is, per se, of conventional form.

The actuating linkage preferably comprises a shaft fixedly mounted from the handle, with a longitudinal groove or hole receiving an actuating rod and mounting the tip portion at the distal end of the shaft.

The tip portion comprises an assembly of relatively moveable components usually defined as an inner tip and outer tip. As applied to a surgical punch, the inner tip literally moves within an envelope largely defined by an outer tip. As to scissors and the like the nomenclature is more arbitrary.

In one form of the invention, a single "inner" tip moves while a single "outer" tip is stationary. In some applications a single "inner" tip would move, while a single "outer" tip would be stationary. The tip assembly is operated to excise tissue in bits, to separate one piece of tissue from another, to grasp and/or manipulate and/or remove particulate matter. The tip assembly has a pivotal mounting with a fixed shaft extension of the outer tip integrally formed therewith. The articulating inner tip has a groove seating on the shaft extension to define the pivotal mount. An actuating linkage extends from an actuating system in the handle through an elongated channel of the probe and terminating in a connection at the inner tip offset from the pivotal mount to provide a levering articulation motion to the inner tip forward and back between 'upper' and 'lower' positions. In case of breakage in use, each of the inner and outer tip retains its basic shape and neither generates small break-off pieces. Further, the inner and outer tip retain their assembly to each other and assembled to the probe relationships and a significant degree of their operability.

The invention accommodates the direct articulating drive to the inner tip as well as related actions of proper use, e.g. twisting and pulling or pushing of the instrument as a whole, and improper uses.

Positive stops are provided to prevent the inner tip from escaping from its nested relation with the outer tip.

The integral pivot extension of the outer tip which forms the pivot mount preferably has an hour-glass shape which does not weaken the adjacent outer tip wall(s), but rather enhances strength and rigidity of the same. The integral pivot enables thinner wall sections of the outer tip and shaving the design of 'upper' and 'lower' edges (hereinafter shown) of the outer tip to be closer to the pivot center and maximize engagement of tissue or other material or objects to be grasped.

In a second form of the invention, the tip portion comprises an assembly of relatively moveable components usually defined as two opposed movable inner tips and fixed side walls for the tips in 'closed' position nested therein, with one movable inner tip being essentially a mirror image of the other. As applied to a surgical punch of the type used in laparoscopic surgery, the inner tips can be arranged to intersect in a scissor fashion to sever tissue. As to a grasper, the inner tips can be arranged to abut each other in a grasper fashion to restrain or excise tissue. The inner tips of the grasper may also have intersecting cups to aid in the above grasping function.

The movable inner tips when closed are nested between fixed side walls which comprise extensions of a fixed tubular probe shaft. Each inner tip has a groove seating on a pivotal mount which is formed integrally with the shaft extensions. An actuating linkage extends from an actuating system in the handle through an elongated channel of the tubular probe and terminating in a connection at each inner tip offset from the pivotal mount to provide a levering articulation motion to each inner tip forward and back between its 'open' and 'closed' positions.

The integral pivot extension of the sidewall extensions, which form the pivot mount, preferably has a dual hour-glass form which does not weaken the adjacent extension tip wall(s), but rather enhances strength and rigidity of the same. One or more further hourglass spans (of single or dual hourglass form) are provided behind the pivot mount span.

Other objects, features, and advantages will be apparent from the following detailed description of preferred embodiments taken in conjunction with the accompanying drawing in which:

BRIEF DESCRIPTION OF THE DRAWINGS

FIGS. 9 and 10 are side and top views of one of the moveable inner tips of the FIGS. 6-8 embodiment showing a channel with inverse hour glass design to mate with the fixed pivot of the side walls span (formed integrally with those walls).

FIG. 9A is a cross-sectional view taken generally along the pane defined by reference line 9A—9A of FIG. 9 and showing the toothed end portion of that tip.

FIG. 9B is a cross-sectional view of a portion of the tip channel showing its conformation to the pivotal mount.

FIG. 10 is a top view of the structure shown in FIG. 9.

FIG. 14 is an exploded side view of certain components of the embodiment shown in FIGS. 6-13.

FIG. 15 is a similar exploded top view of the structure shown in FIG. 14.

DETAILED DESCRIPTION OF PREFERRED EMBODIMENTS

Figure 1:
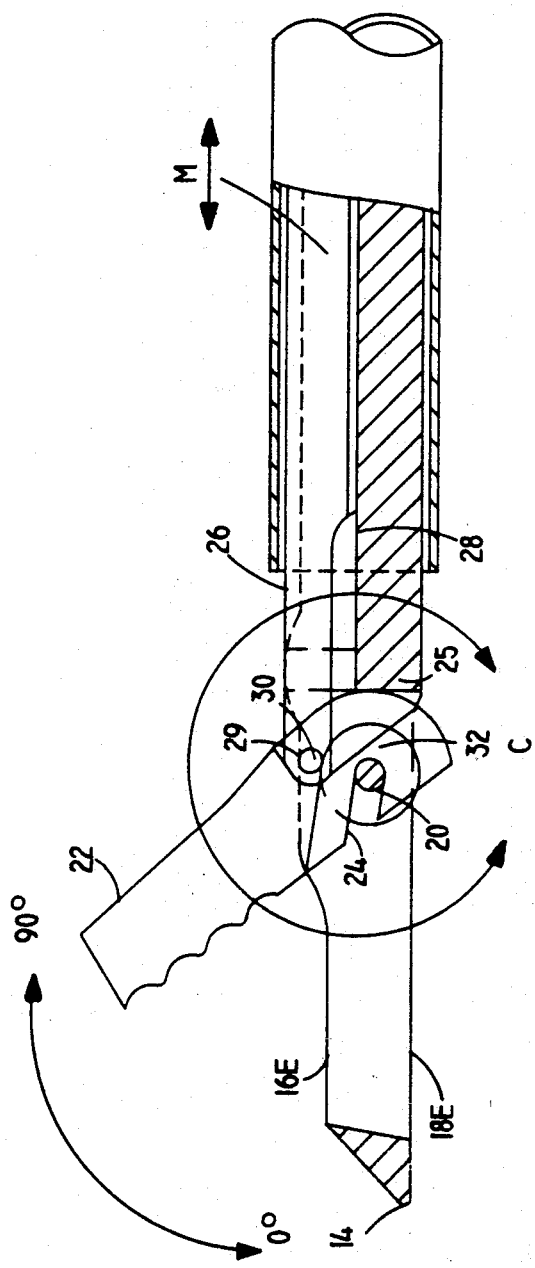
FIG. 1 is a side view taken generally along the plane defined by reference line 1—1 of FIG. 2, showing a probe end of a preferred embodiment of the invention applied to a punch utilization with a supplementary diagram, wherein the inner tip is shown in partially open position with an adjacent arrow indicating the relative range of motion.
Figure 2:
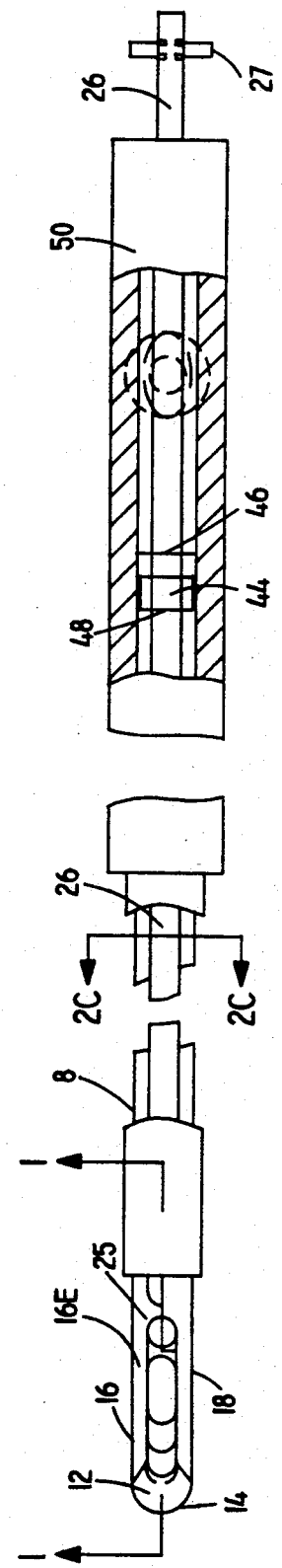
FIG. 2 is a top view of the probe end of FIG. 1.

The side view/top view assembly drawings of FIGS. 1-2 (and ancillary views FIGS. 1A, 1B, 2A, 2B and 2C including sections and views taken as indicated at A—A in FIG. 2 for FIG. 1, B—B for FIG. 2C, View C in FIG. 1 for FIG. 1A, D—D and E—E of FIG. A for FIGS. 1B and 2A and F—F of FIG. 1A for FIG. 2B) show an endoscopic punch of a type used in TMJ surgical procedures. The punch has an elongated probe 8 (FIG. 2) with an outer tip 12 of U-shape form with an end 14 and sidewalls 16 and 18 with upper and lower cutting edges 16E and 18E (FIG. 1) and an integral pivot 20 of essentially hourglass form integrally formed with and bridging the walls 16 and 18. An inner tip 22 is mounted on the pivot for rotation as indicated by the double arrow shown in FIG. 1 between an open position (FIG. 1) and a closed position nested within the outer tip. A channel or slot 24 of the inner tip seats on the integral pivot of the outer tip. The channel is shaped with a negative hourglass at its base to conform to the positive hourglass form of the integral pivot 20. The internal centerlines of the positive and negative hourglass forms are coincident. The inner tip's range of arcuate movement brings its upper face to bear on surface 25 of the outer tip. Ramp surface 25 is dimensioned to allow necessary opening rotary motion, but restrict disengagement linear motion of the pivot elements.

The upper portion of the inner tip, above the channel, has a cross-hole 29. This cross hole accommodates a stud 30 that is an integral pivot extension of a linearly moveable actuating link 26, moveable as indicated by arrow M, riding in a channel 28 and coupled to the inner tip by said stud 30 that passes through cross-hole 29 in the tip, to drive the inner tip between end positions.

The inner tip has a cut out recess 32 to accommodate the rounded end of link 26. As shown in FIGS. 2B, 2A, 1A and 1 the linear movement of link 26 is transmitted via stud 30 to the inner tip to move the inner tip through an arc of up to 90 degrees. The inner tip recess includes a front wall 34 that absorbs part of the actuating force applied through link 26 as inner tip 22 is moved counter clockwise against resistant tissue.

Figure 3:
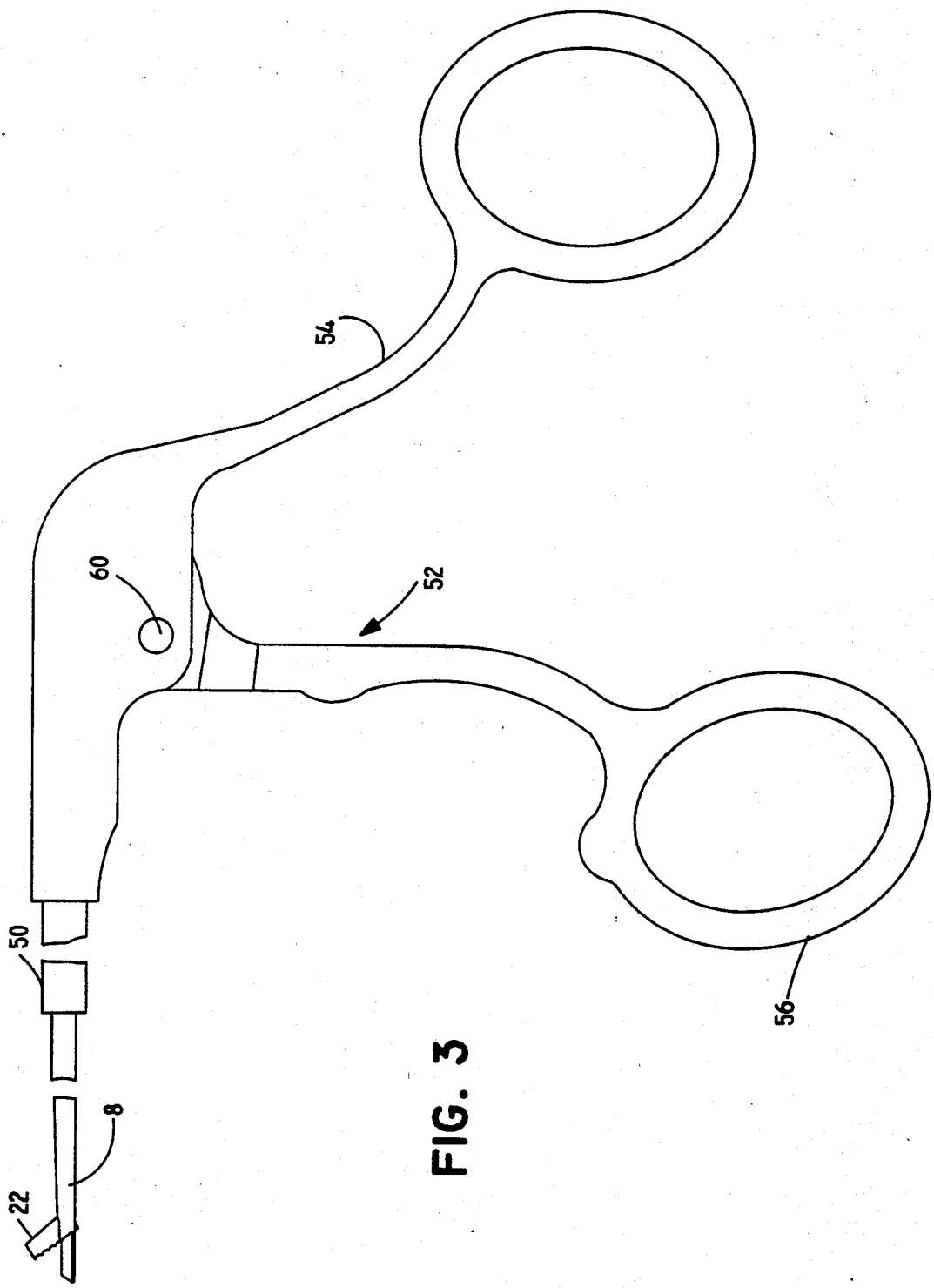
FIG. 3 is a side view of the instrument's handle portion in open position, showing the handle and front end assembled in the open opposition.

At the handle end, stopping is also controlled by a stop block 44 (FIG. 2) on link 26, moveable for distance M between stop faces 46 and 48 of a wide cutout or slot in the bottom of channel 28. A bushing 50 carries probe 8. The bushing is, in turn, encased in a handle assembly 52 (FIG. 3) comprising a thumb loop 54 and a finger loop 56 pivoted at fulcrum 60. The top of the finger loop above the fulcrum has an axial slot 56-1 and cross slots 56-2, 56-3 forming a fork to receive a cross pin 27 (FIG. 2) through the actuating linkage, thus allowing movement of the finger loop to impart driving force M to the actuator linkage.

Figure 4:
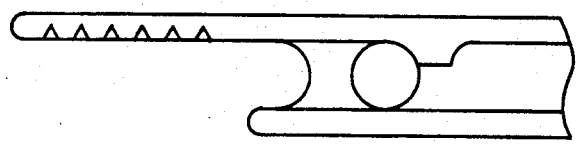
FIGS. 4 and 5 are top views of outer tip variants for the scissors and grabber usage embodiment, respectively.
Figure 5:
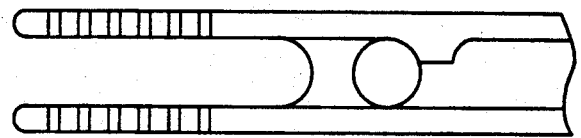

FIG. 4 is a partial top view of the outer tip end 4-12 of an alternative scissors embodiment with side walls 4-16 and 4-18 bridged by an integral pivot 4-20, exemplifying the strengthening ability of this basic pivot. An inner tip mounts on the pivot in the same manner as shown in FIGS. 1 and 2. FIG. 5 is a partial top view of the outer tip end 5-12 of an alternative grabber embodiment with side walls 5-16 and 5-18 bridged by an integral pivot 5-20. An inner tip mounts on the pivot in the same manner as shown in FIGS. 1 and 2.

Figure 1A:
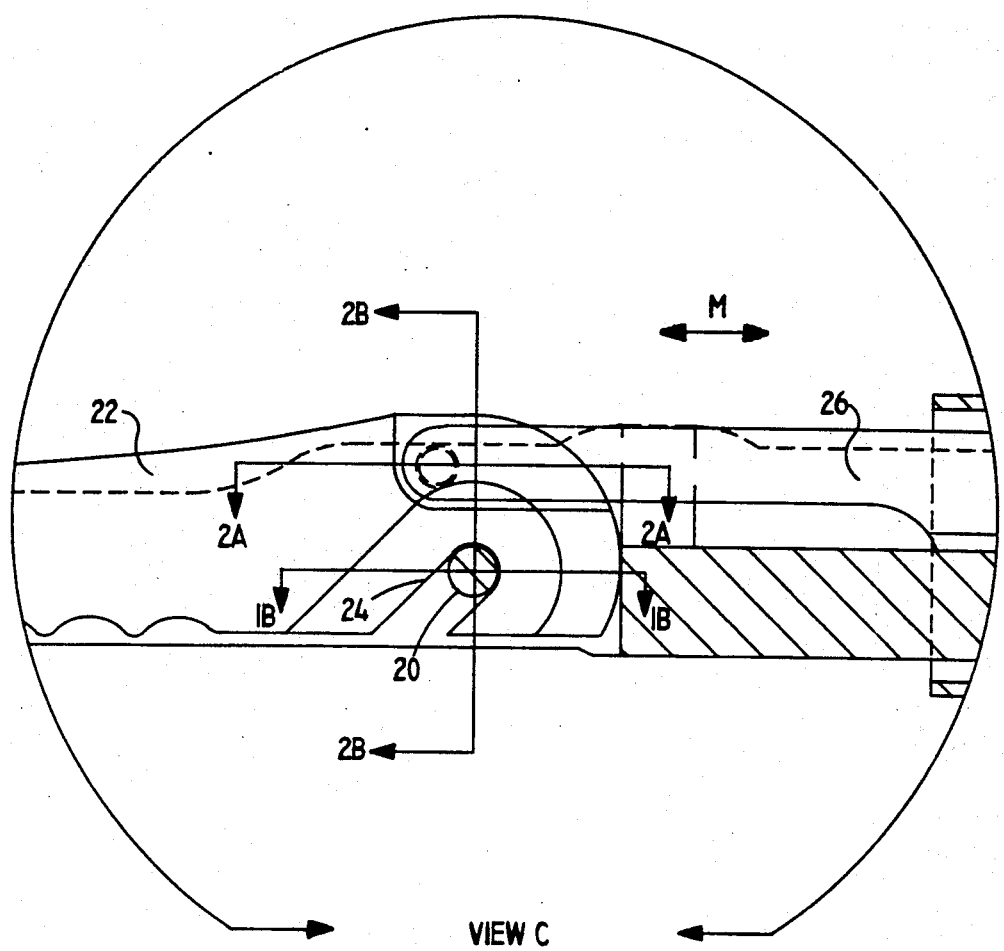
FIG. 1A is a detail view of area C of FIG. 1 showing the relative position of fixed and movable pivots.
Figure 2B:
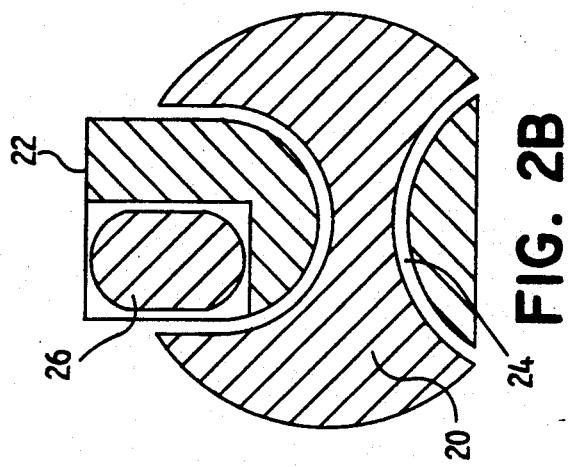
FIG. 2B is a cross-sectional view taken generally along the plane defined by reference line 2B—2B showing the inner tip positioned within the outer tip and showing the movable actuator link nested in the inner tip recess.
Figure 2A:
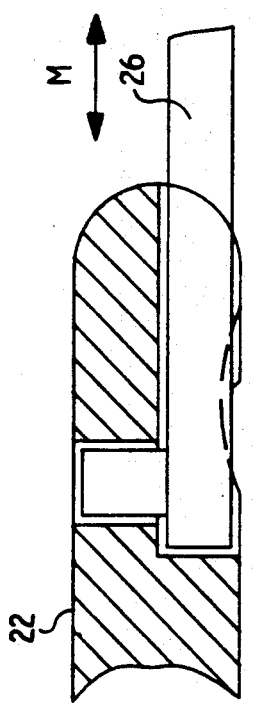
FIG. 2A is a cross-sectional view taken generally along the plane defined by reference line 2A-2A showing movable pivot detail.
Figure 1B:
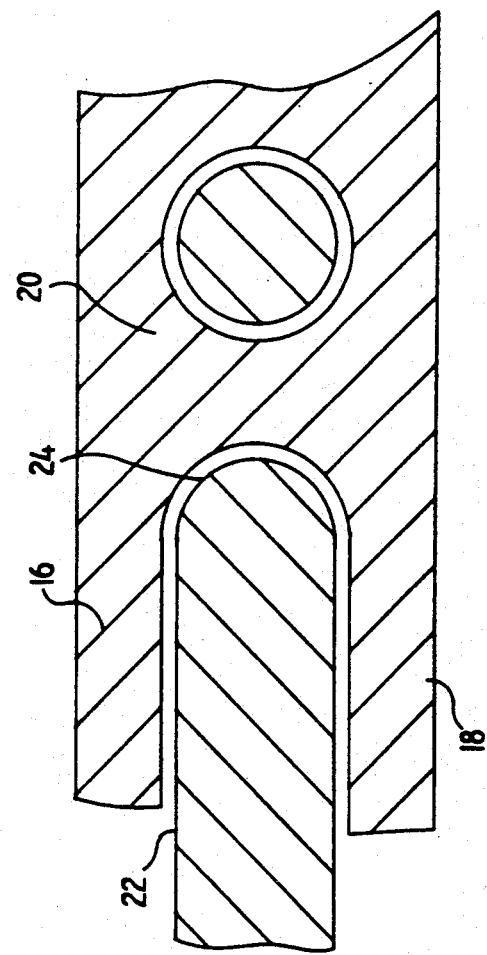
Figure 2C:
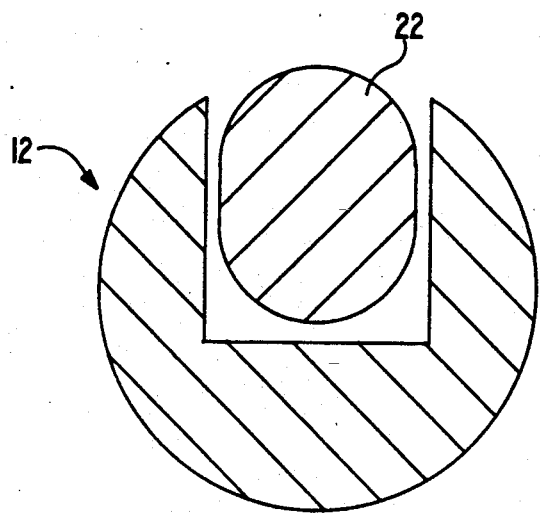
FIG. 2C is a cross-sectional view taken generally along the plane defined by reference line 2C—2C showing the movable actuator link nested in the outer tip slot.

In manufacture, the integral pivot 20 can be made by profiling with a ball end mill cutter into the metal stock of a solid outer tip blank, the cutter being advanced in the directions indicated by arrows M1 and M2 in FIG. 1A. The cut-out area up to surface 25 allows entry of a cutter advanced as indicated by arrow M2 and also allows for inner tip 22 assembly/disassembly with respect to outer tip 12 and pivot 20.

The machined integral pivot shares the metallurgical and strength/toughness characteristics of side walls 16 and 18 of the outer tip 12, whereas welding and other attachment methods would alter and undermine such characteristics within a pivot-tip assembly. The machined integral pivot has, as a natural part of its design, a strength enhancing fillet form at its joinders with the side walls which would not be feasible in a microwelded construction.

Figure 1E:
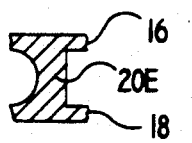
FIGS. 1B, 1BB, 1C, 1D and 1E are cross-sectional partial top views showing fixed pivot detail according to several embodiments of pivot structure, all based on a section taken generally along the plane defined by reference line 1B—1B in FIG. 1A.
Figure 1B:
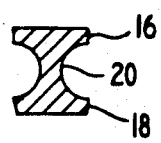
Figure 1C:
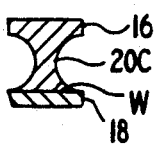
Figure 1D:
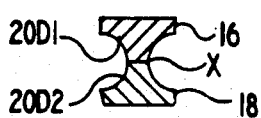

Several variations of the pivot 25 construction are illustrated in FIGS. 1BB, 1C, 1D, 1E. FIG. 1BB shows in sketch form the same pivot 20 as in FIGS. 1, 1A, 2, 2A, 2B, 3 and 4—a full hourglass, fully integral extension of walls 16 and 18. FIG. 1C indicates a partial hourglass pivot 20C integral with one wall 16, but bonded (e.g. welded) at line or to the other wall 18, i.e. non-integral therewith. FIG. 1D shows partial hourglass construction of pivot portions 20D1, 20D2, integral with walls 16 and 18 respectively. FIG. 1C shows a pivot 20E integral of partial hourglass form (a flat machined on one side thereof [or multiple flats]) but integral to both of walls 16, 18. Some of these variations can be combined, e.g. those of FIGA. 1D and 1E. The pivot variations will usually be less desirable than the FIG. 1, 1A, 1B, 1BB construction, but may be tolerable in some applications and will enjoy at least a portion of the advantages described above relative to state of the prior art constructions using a pin or screw as the pivot.

A further preferred embodiment is shown at FIGS. 6–17A.

Figure 7:
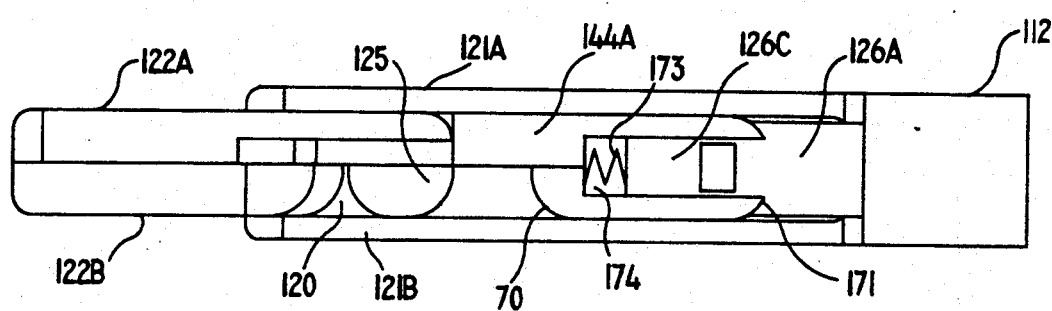
FIG. 7 is a top view of the probe end of FIG. 6.
Figure 6:
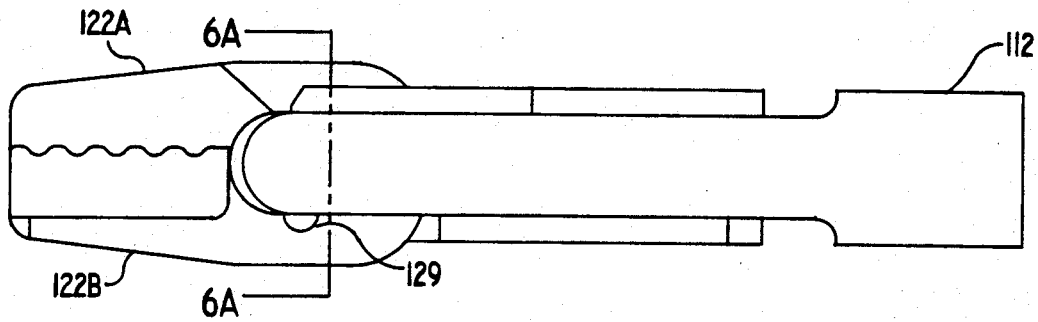
FIG. 6 is a side view of a probe end of a further preferred embodiment of the invention applied (illustratively) to an endoscopic surgical punch with two movable tips of a type used in laparoscopic surgical procedures (and similarly applicable to other instrument and tools.

The side view/top view assembly drawings of FIGS. 6–7 (and ancillary view, FIG. 6A, of a pivot mount component thereof taken as indicated at J—J in FIG. 6) show the distal end of a probe 12' of an endoscopic punch of a type used in laparoscopic surgical procedures. The punch has a two moveable inner tips 122A and 122B (FIG. 6) arranged to intersect in scissor fashion to sever tissue. The tips can also be arranged to abut each other in a grasper function to restrain or excise tissue. The grasper may also have intersecting cups to aid in the grasping function.

Figure 8:
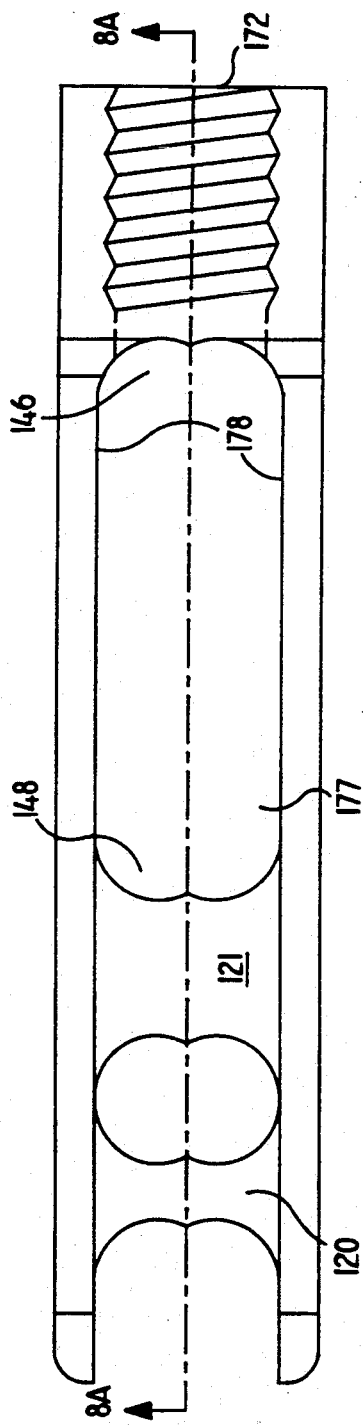
FIG. 8 is a top view of the fixed tubular shaft extension portion of the (probe) of the FIGS. 6-7 embodiment showing the relative positions of the sidewalls spanning pivot mount of dual hour glass design, the machined slot in the probe end behind the pivotal mount for nesting of actuating links therein, with front and rear striking surfaces, and the proximal-end axial hole to receive the actuator rod and support tube.

Referring to FIGS. 6A, 8, 8A and 10, it is shown that the moveable tips are mounted on a fixed pivot 120 of dual hourglass form 20 (FIG. 8). Each tip has a channel 24 (FIG. 9) with an inverse hour glass form (FIG. 9B) to mate with the fixed pivot 120.

Figure 6A:
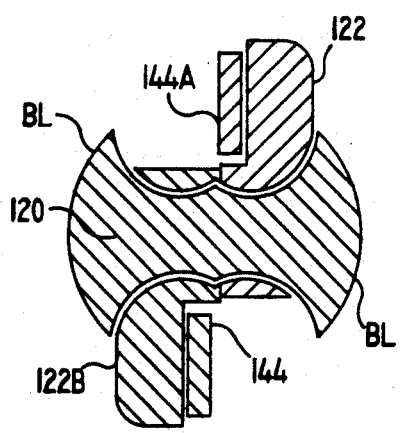
FIG. 6A is a cross-sectional view taken generally along the plane defined by reference line 6A—6A of FIG. 6, and showing the movable inner tips positioned within the fixed outer surround wall and showing the movable actuator links nested in the inner tip recesses, and using parts of the first embodiment (e.g., the general actuating structure of FIG. 3) except where otherwise stated or shown.

The fixed pivot is integrally formed with side wall extensions. Each of the moveable inner tips (122A and 122B) is mounted on the pivot for rotation between an open position and a closed position nested between the side walls (FIG. 6A). A channel or slot 124 of each inner tip seats on a portion of the fixed integral pivot. The channel is shaped with a negative hourglass at its base to conform to one of the two positive hourglass forms of the fixed pivot. Letters BL remind the viewer that the edges of 120 are only break lines, a drafting artifact, not ends or edges of the pivot.

Figure 6B:
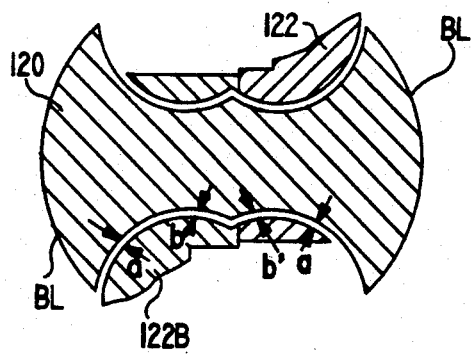
FIG. 6B is an expansion of FIG. 6A showing variant of gap profile in the FIG. 6-7 embodiment (in an unloaded position).

FIG. 6B, an expansion of FIG. 6A illustrates the point that when a double hourglass form of pivot is used, the gap dimension a (when the instrument articulating tips are not under load) is less than gap b and fractions of the (a—b) differential occur between the locations of arrows a and b; typically 0.001"–0.002" differential between a and b. This occurs because the ball end mill cutter used to form the hourglass form(s) encounters greater rigidity (resistance) adjacent the walls 121A, 121B and renders an unbalanced cutting of the hourglass profile to that extent. However, the result is beneficial since the biassed reaction forces provided thereby lead to an optional nesting of the two articulating inner tips 122A, 122B which thereby have a force tending to keep them in adjacent sliding relation to each other under loaded (extension, working, detraction) conditions.

The variants shown and described above at FIGS 1C, 1D, 1E and related specification text, above, may be applied to the FIGS. 6, 6A, 6B, 7-17 embodiment.

The probe's proximal end has an axial hole 72 (FIG. 8) to receive an actuator rod and support tube therefor. The support tube may be threaded with either internal or external threads and then screwed to the mating threads 12T on the probe.

Figure 8A:
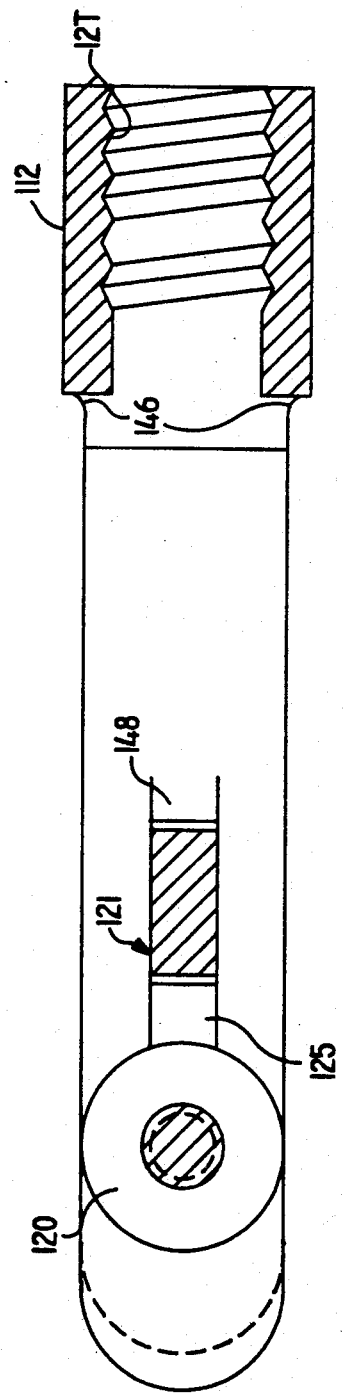
FIG. 8A is a cross-sectional view taken generally along the plane defined by reference line 8A-8A of FIG. 8 and showing fixed-pivot and ramp surface detail.
Figure 13:
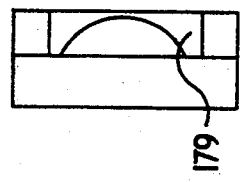
FIGS. 11, 12 and 13 are are side, top and end views, respectively, of the connecting link between each moveable inner tip and the actuating linkage, showing the rounded distal-end with stud extension for nesting with the cross-hole in the inner tip, and the flag-shaped proximal-end for nesting with the slot in the fixed extension of the probe.
Figure 12:
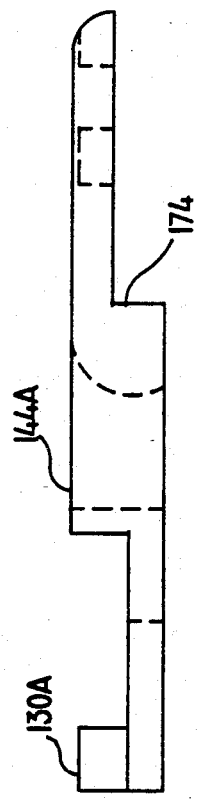
Figure 11:
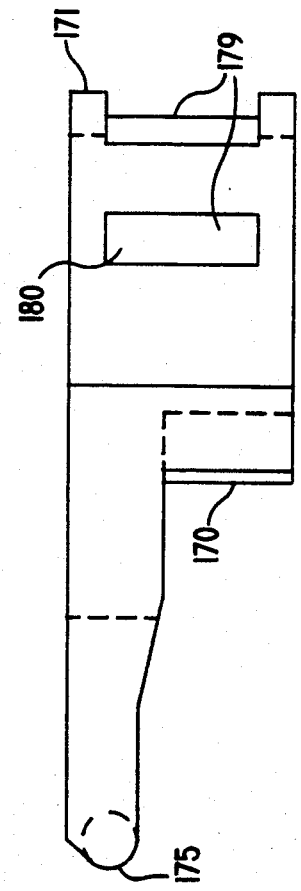
Figure 16:
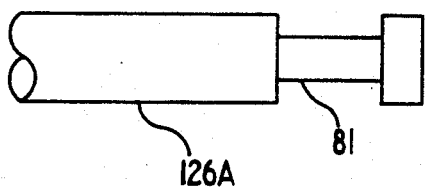
FIG. 16 is an elevational view showing the proximal-end of the actuator rod having a reduced section to nest with a mating bore in an upper pivot portion of a finger loop of a scissors actuator.

Each inner tip has a cross-hole 129 (FIG. 9). This cross hole accommodates a stud 130A (FIG. 12) that is an integral extension of the rounded distal-end of a linearly moveable connecting link 144A (FIG. 12), coupled to the inner tip by said stud and cross-hole. The proximal-end of said link 144A is flag shaped (FIGS. 11–13) and is nested in a slot 177 (FIG. 8) machined in the probe behind ramp surface 25 (FIG. 8A).

Each inner tip's range of arcuate movement brings its upper face to bear on the said ramp surface 125 of an integral bridging strip 121C of the outer wall assembly. Ramp surface 125 is dimensioned to allow necessary opening rotary motion, but restrict disengagement linear motion of the pivot elements. Surfaces 146 and 148 (FIG. 8) of slot 77 limit the linear motions of links 144A and 144B (FIG. 7). In the nested positions of the tips, the links are opposed and the flags are overlapping to accommodate the relative positions of the moveable tips. The walls 78 of slot 77 (FIG. 8) restrict disengagement lateral motion of the links. The machined geometry restricts the links to linear motion and some rotational motion with respect to each other.

The links have parallel circular channels 179 (FIG. 11) machined into the inside surface of their flag portions perpendicular to the longitudinal axis of the instrument. The T-shaped portion 126D FIG. 15) of the actuator rod 126A is inserted through channel 179 and into channel 180 (FIG. 11) of link 144A for example, and rotated one-quarter turn. To prevent accidental disassembly by reverse rotation of the actuator rod, the actuator rod is secured by spring 173 (FIG. 14) and loaded locking mechanism 126C (FIG. 14). The T-shaped portion of the actuator rod nests in channel 126E (FIG. 14) of the locking mechanism. The locking mechanism is nested within machined channels 74 (FIG. 12) to prevent the locking mechanism from rotating.

Figure 17A:
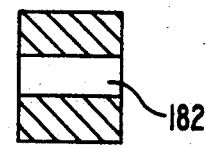
FIG. 17A is a cross-sectional view taken generally along the plane defined by reference line 17A—17A of FIG. 17 showing the groove.
Figure 17:
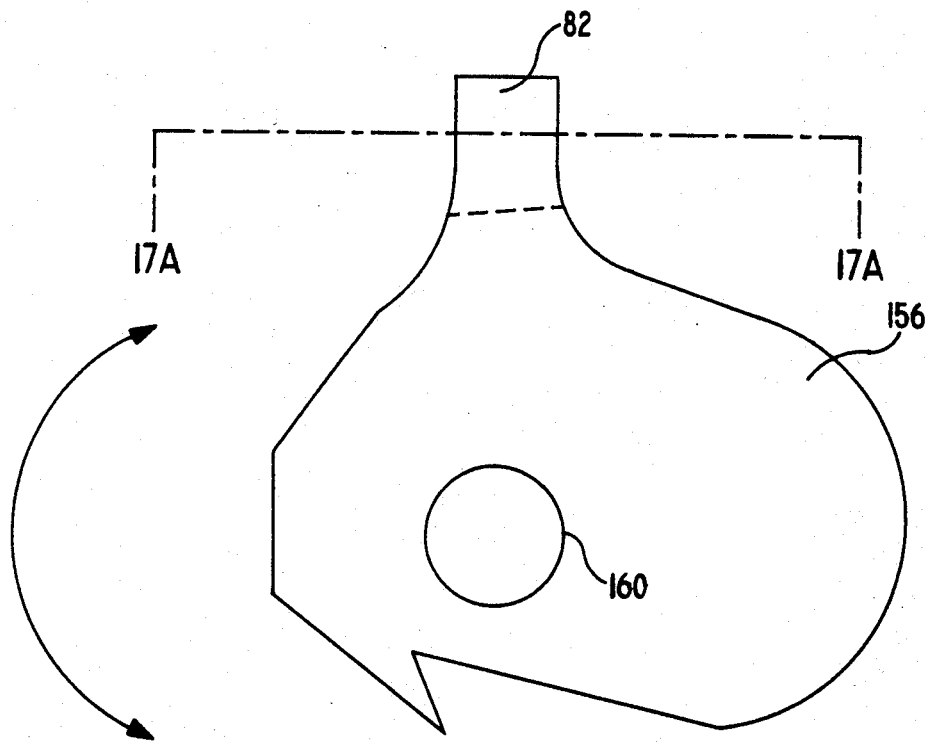
FIG. 17 is an elevational view of the finger loop upper pivot portion.

The proximal-end of the actuator rod 26A (FIG. 16) can be connected to the actuator 156 (FIG. 17). As an alternate construct, a channel 181 (FIG. 16) in the actuator rod would fit into a mating channel 82 (FIG. 17) in the actuator.

In manufacture, a circular rotary cutting tool on a movable mount which itself can be translated in a planetary circular or linear motion is used to form the integral dual hourglass pivot 120, slot 177, and bridge strip 121C including surfaces 125, 146, 148 and walls 178 and their distal extensions 121A and 121B out of a solid rod (before or after boring and tapping hole 72 therein).

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A miniature articulated tip tool comprising:
(a) means defining an articulated tip assembly with at least one pivotable element and a pivot element therefor with a range of movement between extended and retracted positions for effecting selective user controlled pivotal working movements, the said tip assembly comprising at least one wall with an integrally formed extension thereof serving as said pivot element,
(b) means defining a user control handle-actuating system,
(c) means defining an elongated linkage between the handle-actuating system and the articulatable tip pivotable member and a channel including such elongated linkage, the tip having two opposed movable elements on the same pivot, the pivot being of essentially dual hourglass form and the movable elements each having channels of inverse hourglass form conforming to respective hourglass pivot sections.

2. The tool of clam 1 further including means for configuring said tool as an endoscopic surgical instrument.

3. The tool of claim 2 further including means for configuring said tool as a grasper.

4. The tool of claim 2 further including means for configuring said tool as a punch.

5. The tool of claim 2 further including means for configuring said tool as a scissors.

6. The tool of claim 2 wherein the fixed tip has a construction of two side walls with said pivot constituting an integral extension of both.

7. The tool of claim 1 wherein said sidewalls are essentially parallel and the integral pivot has essentially a dual hour glass form.

8. The tool of claim 1 wherein said pivotable elements each have a channel opening of inverse hour glass form conforming to a portion of the integral pivot.

9. The tool of claim 1 constructed and arranged wherein the two channel-pivot conformations comprise gaps, when the instrument is unloaded, that expand going from adjacent walls toward the middle of the pivot.

10. A miniature articulated tip tool comprising:
(a) means defining an articulated tip assembly with at least one pivotable element and a pivot element therefor with a range of movement between extended and retracted positions for effecting selective user controlled pivotal working movements, the said tip assembly comprising at least one wall with an integrally formed extension thereof serving as said pivot element,
(b) means defining a user control handle-actuating system,
(c) means defining an elongated linkage between the handle-actuating system and the articulatable tip pivotable member and a channel including such elongated linkage, the tip assembly having a construction of two side walls with said pivot constituting an integral extension of both, said sidewalls being essentially parallel and the integral pivot has essentially an hour glass form, each said pivotable element having a channel essentially of inverse hour glass form conforming to the pivot.

* * * * *